United States Patent
Sugimoto

(10) Patent No.: US 10,376,523 B2
(45) Date of Patent: Aug. 13, 2019

(54) AQUEOUS COMPOSITION CONTAINING RIPASUDIL, OR A SALT, OR A SOLVATE THEREOF

(71) Applicant: KOWA COMPANY, LTD., Nagoya-shi (JP)

(72) Inventor: Shin Sugimoto, Fuji (JP)

(73) Assignee: KOWA COMPANY, LTD., Nagoya-shi (JP)

( * ) Notice: Subject to any disclaimer, the term of this patent is extended or adjusted under 35 U.S.C. 154(b) by 0 days.

(21) Appl. No.: 15/514,259

(22) PCT Filed: Sep. 25, 2015

(86) PCT No.: PCT/JP2015/077013
§ 371 (c)(1),
(2) Date: Mar. 24, 2017

(87) PCT Pub. No.: WO2016/047719
PCT Pub. Date: Mar. 31, 2016

(65) Prior Publication Data
US 2017/0290841 A1 Oct. 12, 2017

(30) Foreign Application Priority Data

Sep. 25, 2014 (JP) ................. 2014-194679

(51) Int. Cl.
| | | |
|---|---|---|
| A61K 31/551 | (2006.01) | |
| A61K 47/18 | (2017.01) | |
| A61K 9/08 | (2006.01) | |
| A61P 27/02 | (2006.01) | |
| A61K 9/00 | (2006.01) | |
| A61K 31/435 | (2006.01) | |
| A61K 33/42 | (2006.01) | |

(52) U.S. Cl.
CPC .......... *A61K 31/551* (2013.01); *A61K 9/0048* (2013.01); *A61K 9/08* (2013.01); *A61K 31/435* (2013.01); *A61K 33/42* (2013.01); *A61K 47/18* (2013.01)

(58) Field of Classification Search
CPC .............. A61K 31/4725; A61K 31/551; A61K 9/0048; A61K 47/18
USPC ........................................................ 546/139
See application file for complete search history.

(56) References Cited

U.S. PATENT DOCUMENTS

| | | | | |
|---|---|---|---|---|
| 7,867,999 B1* | 1/2011 | Chen | ...................... | A61K 31/35 514/217 |
| 8,193,193 B2* | 6/2012 | Mizuno | ................ | A61K 31/542 514/218 |
| 8,629,161 B2* | 1/2014 | Mizuno | ................ | A61K 31/551 514/218 |
| 2006/0142270 A1 | 6/2006 | Sugimoto et al. | | |
| 2007/0083021 A1 | 4/2007 | Hidaka et al. | | |
| 2008/0064681 A1 | 3/2008 | Hidaka et al. | | |
| 2009/0082338 A1* | 3/2009 | Mizuno | ................ | A61K 31/551 514/218 |
| 2010/0233287 A1 | 9/2010 | Sugimoto et al. | | |
| 2013/0177655 A1 | 7/2013 | Sugimoto et al. | | |
| 2014/0378441 A1 | 12/2014 | Ishibashi et al. | | |
| 2016/0339018 A1 | 11/2016 | Ishibashi et al. | | |

FOREIGN PATENT DOCUMENTS

| | | | | |
|---|---|---|---|---|
| CN | 101087613 | 12/2007 | | |
| EP | 1818059 | 8/2007 | | |
| EP | 1905452 | 4/2008 | | |
| JP | 2006348028 | * 12/2006 | ........... | A61K 31/496 |
| JP | 4212149 B2 | 1/2009 | | |
| JP | 5557408 B1 | 7/2014 | | |
| WO | WO 2006/068208 A1 | 6/2006 | | |
| WO | WO 2006/115244 A1 | 11/2006 | | |

(Continued)

OTHER PUBLICATIONS

AZOPT(TM) brinzolamide ophthalmic suspension 1%, NDA 20-816, Final printing labeling, Apr. 1, 1998.*

(Continued)

*Primary Examiner* — Irina Neagu
(74) *Attorney, Agent, or Firm* — Oblon, McClelland, Maier & Neustadt, L.L.P.

(57) ABSTRACT

An aqueous composition having an excellent antiseptic effect is provided. An aqueous composition containing:

a compound represented by Formula (1), a salt thereof, or a solvate of the compound or the salt thereof,

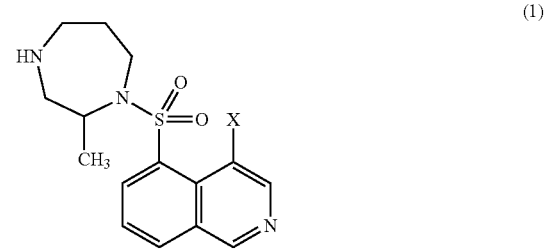

(1)

where X represents a halogen atom, and
a quaternary ammonium surfactant. A method for producing an aqueous composition with an antiseptic effect, by incorporating a compound represented by Formula (1), a salt thereof, or a solvate of the compound or the salt thereof and a quaternary ammonium surfactant into the aqueous composition.

9 Claims, No Drawings

(56) References Cited

FOREIGN PATENT DOCUMENTS

WO  WO2014/010654  1/2014

OTHER PUBLICATIONS

Honda et al. Infection and Drug Resistance 2011, 4, 191-196.*
International Search Report dated Nov. 17, 2015, in PCT/JP2015/077013 filed Sep. 25, 2015.
Ohtake et al., Effects of Ophthalmic Preservative on the Corneal Epithelium, Journal of the Eye, vol. 8, (10), (1991), 7 pages with Partial English Translation.
Isobe, et al., "Effects of K-115, a Rho-Kinase Inhibitor, on Aqueous Humor Dynamics in Rabbits", Current Eye Research, vol. 39, No. 8, (Feb. 6, 2014), ISSN 0271-3683, 11 pages.
Newly Revised Byoki to Yakuzai, Newly Revised $3^{rd}$ Print, Yakuji Hippo Ltd., (Jun. 15, 1986), ISBN4-8408-0066-9, 15 pages with Partial English Translation.
Iyakuhin Interview Form Glanatec® Tengan'eki 0.4%. $6^{th}$ edition, (Jun. 2015), 74 pages with partial English Translation.
Office Action dated Nov. 10, 2017 in Korean Patent Application No. 10-2017-7006791 (with unedited computer generated English translation).
Raymond C Rowe, et al."Handbook of Pharmaceutical Excipients", Pharmaceutical Press, 2003, pp. 45-47.
Hidenobu Tanihara, et al., "Intra-ocular pressure-lower effects of a Rho kinase inhibitor, ripasudil (K-115), over 24 hours in primary open-angle glaucoma an ocular hypertension: a randomized, open-label, crossover study", Acta Ophthalmol. 93(4), e254-e260, Dec. 9, 2014.
Office Action dated Sep. 18, 2018 in Chinese Patent Application No. 201580051331.0 (with English Translation).
An extended European Search Report dated Mar. 27, 2018, in European Patent Application No. 15844047.9.

* cited by examiner

AQUEOUS COMPOSITION CONTAINING RIPASUDIL, OR A SALT, OR A SOLVATE THEREOF

FIELD OF THE INVENTION

The present invention relates to an aqueous composition and the like.

BACKGROUND OF THE INVENTION

A composition containing at least water as a solvent (aqueous composition) is widely used as a drug, a quasi drug, or the like, because of its advantage of having less stimulation in vivo, or being capable of incorporating various components, for example.

Such an aqueous composition, however, has the problem of being susceptible to microbial contamination due to the inclusion of water. In particular, in the case of a dosage form such as an eye drop, a nasal drop, or an ear drop, which is typically repeatedly used, even if a sterilized container or the like is filled with the aqueous composition, it is brought into contact with non-sterile outside air each time of use, which increases the risk of microbial contamination.

Thus, the aqueous composition is typically provided with an antiseptic effect by incorporating an antiseptic (antimicrobial agent) therein. As the antiseptic, a paraben or a quaternary ammonium surfactant such as benzalkonium chloride, for example, is used.

It has been indicated, however, that this antiseptic has a problem such as cytotoxicity (Non Patent Literature 1, for example), and the use of the aqueous composition as an eye drop, for example, may possibly cause corneal injury; therefore, it is desired to minimize the amount of the antiseptic used as much as possible.

In view of this, establishment of a formulation of an aqueous composition having an excellent antiseptic effect through synergistic action of a combination of a plurality of components would enable a corresponding decrease in the amount of each of the antiseptics used alone, and hence, would enable an aqueous composition having higher safety to be provided.

It is known that halogenated isoquinoline derivatives such as ripasudil (chemical name: 4-fluoro-5-[[(2S)-2-methyl-1,4-diazepan-1-yl]sulfonyl]isoquinoline) represented by the following structural formula:

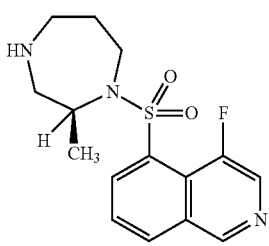 [SMILES: C[C@H]1CNCCCN1S(=O)(=O)c1cccc2cncc(F)c12]

and 4-bromo-5-[[(2S)-2-methyl-1,4-diazepan-1-yl]sulfonyl]isoquinoline represented by the following structural formula:

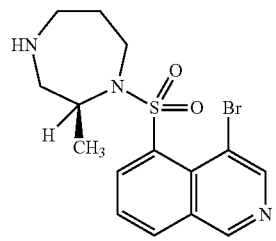 [SMILES: C[C@H]1CNCCCN1S(=O)(=O)c1cccc2cncc(Br)c12]

which have pharmacological action such as Rho kinase inhibitory action (Patent Literatures 1 and 2, for example), have been reported to be useful, for example, as a prophylactic or therapeutic agent for ocular hypertension, glaucoma, and the like (Patent Literature 3, for example), or as a prophylactic or therapeutic agent for ocular fundus diseases such as age-related macular degeneration and the like (Patent Literature 4, for example), and have also been reported as being prepared as an aqueous composition such as an eye drop composition or the like (Patent Literature 3, for example).

However, antiseptic effects of these halogenated isoquinoline derivatives have thus far never been known.

CITATION LIST

Patent Literature

[Patent Literature 1] JP-B-4212149
[Patent Literature 2] WO2006/115244
[Patent Literature 3] WO2006/068208
[Patent Literature 4] JP-B-5557408

Non Patent Literature

[Non Patent Literature 1] Journal of the Eye, 8 (10): 1599-1603, 1991

SUMMARY OF THE INVENTION

Technical Problem

An object of the present invention is to provide an aqueous composition having an excellent antiseptic effect.

Solution to Problem

The present inventor thus conducted extensive research to solve the above-described problem, and surprisingly found that a halogenated isoquinoline derivative represented by Formula (1) shown below, such as ripasudil, has an excellent antiseptic effect, and also found that an aqueous composition having a significantly enhanced antiseptic effect is provided by combining the halogenated isoquinoline derivative with a quaternary ammonium surfactant such as benzalkonium chloride, thus completing the present invention.

In summary, the present invention provides <1> to <4> given below.

<1> An aqueous composition comprising a compound represented by Formula (1):

(1)

wherein X represents a halogen atom,
or a salt thereof, or a solvate of the compound or the salt thereof, and a quaternary ammonium surfactant.

<2> A method for providing an aqueous composition with an antiseptic effect, comprising combining the compound represented by Formula (1), or a salt thereof, or a solvate of the compound or the salt thereof, and a quaternary ammonium surfactant.

<3> A combination of the compound represented by Formula (1), or a salt thereof, or a solvate of the compound or the salt thereof with a quaternary ammonium surfactant, which is used for providing an aqueous composition with an antiseptic effect.

<4> Use of a combination of the compound represented by Formula (1), or a salt thereof, or a solvate of the compound or the salt thereof with a quaternary ammonium surfactant, for providing an aqueous composition with an antiseptic effect.

Effects of Invention

In accordance with the present invention, an aqueous composition having an excellent antiseptic effect and having excellent preservation stability can be provided.

DESCRIPTION OF EMBODIMENTS

The present specification discloses, although is in no way limited to, the following embodiments of invention, by way of example.

[1] An aqueous composition comprising a compound represented by Formula (1):

(1)

wherein X represents a halogen atom,
or a salt thereof, or a solvate of the compound or the salt thereof, and a quaternary ammonium surfactant.

[2] The aqueous composition according to [1], wherein the compound represented by Formula (1) is ripasudil.

[3] The aqueous composition according to [1] or [2], wherein the quaternary ammonium surfactant is at least one selected from the group consisting of benzalkonium chloride and benzethonium chloride.

[4] The aqueous composition according to any of [1] to [3], wherein the compound represented by Formula (1) is ripasudil, and the quaternary ammonium surfactant is benzalkonium chloride.

[5] The aqueous composition according to any of [1] to [4], which is an eye drop or an eye ointment.

[6] The aqueous composition according to any of [1] to [5] (excluding a pharmaceutical for suppressing chronic progressive nephropathy and a film preparation), which is free of phosphoric acid, boric acid, and salts thereof, carbonic anhydrase inhibitors, α1 blockers, and nipradilol.

[7] A method for providing an aqueous composition with an antiseptic effect, comprising combining the compound represented by Formula (1), or a salt thereof, or a solvate of the compound or the salt thereof, and a quaternary ammonium surfactant into an aqueous composition.

[8] The method according to [7], wherein the compound represented by Formula (1) is ripasudil.

[9] The method according to [7] or [8], wherein the quaternary ammonium surfactant is at least one selected from the group consisting of benzalkonium chloride and benzethonium chloride.

[10] The method according to any of [7] to [9], wherein the compound represented by Formula (1) is ripasudil, and the quaternary ammonium surfactant is benzalkonium chloride.

[11] The method according to any of [7] to [10], wherein the aqueous composition is an eye drop or an eye ointment.

[12] The method according to any of [7] to [11], wherein the aqueous composition (excluding a pharmaceutical for suppressing chronic progressive nephropathy and a film preparation) is free of phosphoric acid, boric acid, and salts thereof, carbonic anhydrase inhibitors, α1 blockers, and nipradilol.

[13] The aqueous composition according to any of [1] to [5], further containing at least one selected from the group consisting of α1 receptor blockers, α2 receptor agonists, β blockers, carbonic anhydrase inhibitors, prostaglandin F2α derivatives, sympathomimetics, parasympathomimetics, calcium antagonists, and cholinesterase inhibitors.

[14] The aqueous composition according to any of [1] to [5], further containing at least one selected from the group consisting of latanoprost, nipradilol, dorzolamide, brinzolamide, and timolol, as well as salts thereof.

[15] The method according to any of [7] to [11], wherein an aqueous composition further contains at least one selected from the group consisting of α1 receptor blockers, α2 receptor agonists, β blockers, carbonic anhydrase inhibitors, prostaglandin F2α derivatives, sympathomimetics, parasympathomimetics, calcium antagonists, and cholinesterase inhibitors.

[16] The method according to any of [7] to [11], wherein an aqueous composition further contains at least one selected from the group consisting of latanoprost, nipradilol, dorzolamide, brinzolamide, and timolol, as well as salts thereof.

<<With Regard to the Invention of Embodiments Concerning the Aqueous Composition>>

Hereinafter, the invention of embodiments concerning the "aqueous composition" will be first described in detail, in terms of the meaning of the term, for example.

Examples of the halogen atom in Formula (1) include a fluorine atom, a chlorine atom, and a bromine atom. In Formula (1), a fluorine atom or a bromine atom is preferred as the halogen atom, and a fluorine atom is particularly preferred.

Further, in Formula (1), the carbon atom forming the homopiperazine ring substituted with the methyl group is an asymmetric carbon atom. As a result, stereoisomerism occurs. The compound represented by Formula (1) includes all the stereoisomers, and may be a single stereoisomer or a mixture of various stereoisomers at any given ratio. Preferred as the compound represented by Formula (1) is a compound having the S configuration as the absolute configuration.

The salt of the compound represented by Formula (1) is not particularly limited as long as it is a pharmacologically acceptable salt, and specific examples of the salt include inorganic acid salts such as hydrochloride, sulfate, nitrate, hydrofluoride, and hydrobromide; and organic acid salts such as acetate, tartrate, lactate, citrate, fumarate, maleate, succinate, methanesulfonate, ethanesulfonate, benzenesulfonate, toluenesulfonate, naphthalenesulfonate, and camphorsulfonate, with hydrochloride being preferred.

The compound represented by Formula (1) or a salt thereof may also be in the form of a hydrate or a solvate such as an alcohol solvate, and is preferably in the form of a hydrate.

Specific examples of the compound represented by Formula (1) or a salt thereof or a solvate of the compound or the salt thereof include:

ripasudil (chemical name: 4-fluoro-5-[[(2S)-2-methyl-1,4-diazepan-1-yl]sulfonyl]isoquinoline) or a salt thereof or a solvate of ripasudil or the salt thereof; and 4-bromo-5-[[(2S)-2-methyl-1,4-diazepan-1-yl]sulfonyl]isoquinoline or a salt thereof or a solvate of the compound or the salt thereof.

The compound represented by Formula (1) or a salt thereof or a solvate of the compound or the salt thereof is preferably ripasudil or a salt thereof or a solvate of ripasudil or the salt thereof, or 4-bromo-5-[[(2S)-2-methyl-1,4-diazepan-1-yl]sulfonyl]isoquinoline or a salt thereof or a solvate of the compound or the salt thereof, more preferably ripasudil or a salt thereof or a solvate of ripasudil or the salt thereof, still more preferably ripasudil or a hydrochloride thereof or a hydrate of ripasudil, or the hydrochloride thereof, and particularly preferably a ripasudil hydrochloride hydrate (ripasudil monohydrochloride dihydrate) represented by the following structural formula:

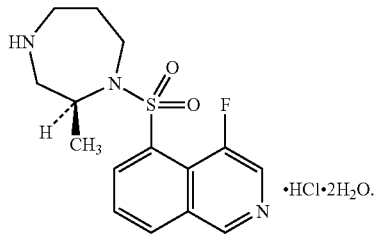 [SMILES: C[C@H]1CNCCCN1S(=O)(=O)c1cccc2cncc(F)c12]

The compound represented by Formula (1) or a salt thereof or a solvate of the compound or the salt thereof is known and can be produced using a known method. Specifically, ripasudil or a salt thereof or a solvate of ripasudil or the salt thereof can be produced using the method described in WO1999/020620 or WO2006/057397, for example. 4-Bromo-5-[[(2S)-2-methyl-1,4-diazepan-1-yl]sulfonyl]isoquinoline or a salt thereof or a solvate of the compound or the salt thereof can be produced using the method described in WO2006/115244, for example.

The content of the compound represented by Formula (1) or a salt thereof or a solvate of the compound or the salt thereof in the aqueous composition is not particularly limited, and may be determined as appropriate, in consideration of the target disease, or the sex, age, or symptoms of the patient, for example. From the viewpoint of achieving an excellent antiseptic effect, however, the content of the compound represented by Formula (1) or a salt thereof or a solvate of the compound or the salt thereof is preferably 0.01 to 10 w/v %, more preferably 0.02 to 8 w/v %, and particularly preferably 0.04 to 6 w/v %, calculated as the free form of the compound represented by Formula (1), based on the total volume of the aqueous composition. In particular, when ripasudil is used as the compound represented by Formula (1), from the viewpoint of achieving an excellent antiseptic effect, the content of ripasudil or a salt thereof or a solvate of ripasudil or the salt thereof is preferably 0.05 to 5 w/v %, more preferably 0.1 to 3 w/v %, and particularly preferably 0.1 to 2 w/v %, calculated as the free form, based on the total volume of the aqueous composition.

Examples of the "quaternary ammonium surfactant" include benzalkonium chloride and benzethonium chloride, which are known as antiseptics. From the viewpoint of achieving an excellent antiseptic effect, the quaternary ammonium-type surfactant is preferably benzalkonium chloride.

Note that quaternary ammonium surfactants are known, and a quaternary ammonium surfactant may be produced using a known method, or a commercially available quaternary ammonium surfactant may be used.

The content of the quaternary ammonium surfactant in the aqueous composition is not particularly limited, and may be determined as appropriate; however, from the viewpoint of achieving an excellent antiseptic effect, the content is preferably 0.00005 to 0.02 w/v %, more preferably 0.00025 to 0.01 w/v %, and particularly preferably 0.00025 to 0.004 w/v %, based on the total volume of the aqueous composition. In particular, when benzalkonium chloride is used as the quaternary ammonium-type surfactant, from the viewpoint of achieving an excellent antiseptic effect, the content is preferably 0.0001 to 0.01 w/v %, more preferably 0.0005 to 0.005 w/v %, and particularly preferably 0.0005 to 0.002 w/v %, based on the total volume of the aqueous composition.

As described in the test examples below, the combination of the compound represented by Formula (1) or a salt thereof or a solvate of the compound or the salt thereof with the quaternary ammonium surfactant exhibits a significantly enhanced antiseptic effect through their synergistic action. Thus, for example, the amount of the quaternary ammonium surfactant used, such as benzalkonium chloride, can also be reduced to provide an aqueous composition with higher safety.

From the viewpoint of augmenting the antiseptic effect through synergistic action, the combination is particularly preferably a combination of ripasudil or a salt thereof or a solvate of ripasudil or the salt thereof with benzalkonium chloride.

The proportion by mass of the quaternary ammonium surfactant relative to the compound represented by Formula (1) or a salt thereof or a solvate of the compound or the salt thereof contained in the aqueous composition is not particularly limited. From the viewpoint of achieving an excellent antiseptic effect, however, the proportion of the quaternary ammonium surfactant is preferably 0.0001 to 0.4 part by mass, more preferably 0.001 to 0.04 part by mass, and particularly preferably 0.00125 to 0.015 part by mass, relative to 1 part by mass of the compound represented by Formula (1) or a salt thereof or a solvate of the compound or the salt thereof as the free form.

In particular, when ripasudil or a salt thereof or a solvate of ripasudil or the salt thereof is used as the compound represented by Formula (1) or a salt thereof or a solvate of the compound or the salt thereof, and benzalkonium chloride is used as the quaternary ammonium surfactant, from the viewpoint of achieving an excellent antiseptic effect, the proportion of benzalkonium chloride is preferably 0.0002 to 0.2 part by mass, more preferably 0.002 to 0.02 part by mass, and particularly preferably 0.0025 to 0.01 part by mass, relative to 1 part by mass of ripasudil or a salt thereof or a solvate of ripasudil or the salt thereof as the free form.

As used herein, the "aqueous composition" means a composition containing at least water, which may be in the form of a liquid (solution or suspension) or a semi-solid (ointment), for example. As the water in the composition, purified water, water for injection, or sterile purified water, for example, can be used.

While the content of water in the aqueous composition is not particularly limited, it is preferably 5 mass % or more, more preferably 20 mass % or more, still more preferably 50 mass % or more, even more preferably 90 mass % or more, and particularly preferably 90 to 99.8 masse.

The aqueous composition can be prepared into various dosage forms in accordance with known methods described in the General Rules for Preparations in the Japanese Pharmacopoeia $16^{th}$ Edition, for example. While the dosage form is not particularly limited, dosage forms include injections, inhalation solutions, eye drops, eye ointments, ear drops, nasal drops, enemas, liquids for external use, sprays, ointments, gels, oral liquids, and syrups. From the viewpoint of advantageously utilizing the pharmacological action of the compound represented by Formula (1), the dosage form is an agent for an eye disease, which specifically is preferably an eye drop or an eye ointment, and is particularly preferably an eye drop.

The aqueous composition may contain, in addition to the components described above, additives used in drugs, quasi drugs, and the like, in accordance with the dosage foam. Examples of such additives include inorganic salts, isotonic agents, chelating agents, stabilizers, pH regulators, antiseptics other than quaternary ammonium surfactants, antioxidants, thickeners, surfactants, solubilizers, suspending agents, cooling agents, dispersants, preservatives, oily bases, emulsion bases, and water-soluble bases.

Specific examples of these additives include ascorbic acid, potassium aspartate, sodium bisulfite, alginic acid, sodium benzoate, benzyl benzoate, epsilon-aminocaproic acid, fennel oil, ethanol, ethylene-vinyl acetate copolymer, sodium edetate, tetrasodium edetate, potassium chloride, calcium chloride hydrate, sodium chloride, magnesium chloride, hydrochloric acid, alkyldiaminoethylglycine hydrochloride solution, carboxyvinyl polymer, dried sodium sulfite, dried sodium carbonate, d-camphor, dl-camphor, xylitol, citric acid hydrate, sodium citrate hydrate, glycerin, gluconic acid, L-glutamic acid, monosodium L-glutamate, creatinine, chlorhexidine gluconate solution, chlorobutanol, sodium dihydrogen phosphate dihydrate, geraniol, sodium chondroitin sulfate, acetic acid, potassium acetate, sodium acetate hydrate, titanium oxide, gellan gum, dibutylhydroxytoluene, potassium bromide, tartaric acid, sodium hydroxide, polyoxyl 45 stearate, purified lanolin, D-sorbitol, sorbitol solution, sorbic acid, potassium sorbate, taurine, sodium bicarbonate, sodium carbonate hydrate, sodium thiosulfate hydrate, thimerosal, tyloxapol, sodium dehydroacetate, trometamol, concentrated glycerin, mixed tocopherol concentrate, white petrolatum, mentha water, mentha oil, ethyl parahydroxybenzoate, butyl parahydroxybenzoate, propyl parahydroxybenzoate, methyl parahydroxybenzoate, sodium hyaluronate, human serum albumin, hydroxyethyl cellulose, hydroxypropyl cellulose, hypromellose, glacial acetic acid, sodium pyrosulfite, phenylethyl alcohol, glucose, propylene glycol, bergamot oil, benzyl alcohol, borax, boric acid, povidone, polyoxyethylene (200) polyoxypropylene glycol (70), sodium polystyrene sulfonate, polysorbate 80, polyoxyethylene hydrogenated castor oil 60, partially hydrolized polyvinyl alcohol, d-borneol, macrogol 4000, macrogol 6000, D-mannitol, anhydrous citric acid, anhydrous sodium monohydrogen phosphate, anhydrous sodium dihydrogen phosphate, methanesulfonic acid, methylcellulose, 1-menthol, monoethanolamine, aluminum monostearate, polyethylene glycol monostearate, eucalyptus oil, potassium iodide, sulfuric acid, oxyquinoline sulfate, liquid paraffin, borneo camphor, phosphoric acid, dibasic sodium phosphate hydrate, potassium dihydrogenphosphate, sodium dihydrogenphosphate, sodium dihydrogenphosphate monohydrate, malic acid, and petrolatum.

Examples of preferred additives include potassium chloride, calcium chloride hydrate, sodium chloride, magnesium chloride, glycerin, acetic acid, potassium acetate, sodium acetate hydrate, tartaric acid, sodium hydroxide, sodium bicarbonate, sodium carbonate hydrate, concentrated glycerin, hydroxyethyl cellulose, hydroxypropyl cellulose, hypromellose, borax, boric acid, povidone, polysorbate 80, polyoxyethylene hydrogenated castor oil, polyethylene glycol monostearate, partially hydrolized polyvinyl alcohol, macrogol 4000, macrogol 6000, anhydrous citric acid, anhydrous sodium monohydrogen phosphate, anhydrous sodium dihydrogen phosphate, methylcellulose, monoethanolamine, phosphoric acid, dibasic sodium phosphate hydrate, potassium dihydrogenphosphate, sodium dihydrogenphosphate, sodium dihydrogenphosphate monohydrate, sodium hyaluronate, glucose, and 1-menthol.

The aqueous composition may further contain, in addition to the components described above, other medicinal components in accordance with the target disease and the like. Examples of such medicinal components include al receptor blockers including bunazosin or a salt thereof or a solvate of bunazosin or the salt thereof, such as bunazosin hydrochloride; α2 receptor agonists including brimonidine or a salt thereof or a solvate of brimonidine or the salt thereof, such as brimonidine tartrate, and apraclonidine or a salt thereof or a solvate of apraclonidine or the salt thereof; p blockers including carteolol or a salt thereof or a solvate of carteolol or the salt thereof, such as carteolol hydrochloride, nipradilol or a salt thereof or a solvate of nipradilol or the salt thereof, timolol or a salt thereof or a solvate of timolol or the salt thereof, such as timolol maleate, betaxolol or a salt thereof or a solvate of betaxolol or the salt thereof, such as betaxolol hydrochloride, levobunolol or a salt thereof or a solvate of levobunolol or the salt thereof, such as levobunolol hydrochloride, befunolol or a salt thereof or a solvate of befunolol or the salt thereof, and metipranolol or a salt thereof or a solvate of metipranolol or the salt thereof; carbonic anhydrase inhibitors including dorzolamide or a salt thereof or a solvate of dorzolamide or the salt thereof, such as dorzolamide hydrochloride, brinzolamide or a salt thereof or a solvate of brinzolamide or the salt thereof, acetazolamide or a salt thereof or a solvate of acetazolamide or the salt thereof, dichlorphenamide or a salt thereof or a solvate of dichlorphenamide or the salt thereof, and methazolamide or a salt thereof or a solvate of methazolamide or the salt thereof; prostaglandin F2α derivatives including isopropyl unoprostone or a salt thereof or a solvate of isopropyl unoprostone or the salt thereof, tafluprost or a salt thereof or a solvate of tafluprost or the salt thereof, travoprost or a salt thereof or a solvate of travoprost or the salt thereof, bimatoprost or a salt thereof or a solvate of bimatoprost or the salt thereof, latanoprost or a salt thereof or a solvate of latanoprost or the salt thereof, cloprostenol or a salt thereof or a solvate of cloprostenol or the salt thereof, and fluprostenol or a salt thereof or a solvate of fluprostenol or the salt thereof; sympathomimetics including dipivefrine or a salt thereof or a solvate of dipivefrine or the salt thereof, such as dipivefrine hydrochloride, and epinephrine or a salt thereof or a solvate of epinephrine or the salt thereof, such as epinephrine, epinephrine borate, or epinephrine hydrochloride; parasympathomimetics including distigmine bromide or a salt thereof or a solvate of distigmine or the salt thereof, pilocarpine or a salt thereof or a solvate of pilocarpine or the salt thereof, such as pilocarpine, pilocarpine hydrochloride, or pilocarpine nitrate, and carbachol or a salt thereof or a solvate of carbachol or the salt thereof; calcium antagonists including lomerizine or a salt thereof or a solvate of lomerizine or the salt thereof, such as lomerizine hydrochloride; and cholinesterase inhibitors including demecarium or a salt thereof or a solvate of demecarium or the salt thereof, echothiophate or a salt thereof or a solvate of echothiophate or the salt thereof, and physostigmine or a salt thereof or a solvate of physostigmine or the salt thereof. One or more of these medicinal components can be incorporated.

Preferred as the other medicinal components is at least one selected from the group consisting of latanoprost, nipradilol, dorzolamide, brinzolamide, and timolol, as well as salts thereof.

The pH of the aqueous composition is not particularly limited, but is preferably from 4 to 9, more preferably from 4.5 to 8, and particularly preferably from 5 to 7. The osmotic pressure ratio of the aqueous composition relative to physiological saline is not particularly limited, but is preferably from 0.6 to 3, and particularly preferably from 0.6 to 2.

The aqueous composition is preferably housed in a container, from the viewpoint of its preservation stability, portability, and the like. The form of the container is not particularly limited as long as the aqueous composition can be housed, and may be selected and set as appropriate, in accordance with the dosage form, for example. Specific examples of such forms of the container include containers for injections, containers for inhalations, containers for sprays, bottle-shaped containers, tubular containers, containers for eye drops, containers for nasal drops, containers for ear drops, and bag containers. Further, these containers may also be packaged in a box or a bag, for example.

The material of the container is not particularly limited, and may be selected as appropriate depending on the form of the container. Specific examples of materials include glass, plastics, cellulose, pulp, rubber, and metals. The material of the container is preferably a plastic, from the viewpoint of processability, squeezability, durability, and the like. The resin of the container made of a plastic is preferably a thermoplastic resin. Examples of such resins include polyolefin-based resins such as low-density polyethylene (including linear low density polyethylene), high-density polyethylene, medium-density polyethylene, polypropylene, and cyclic polyolefins; polyester-based resins such as polyethylene terephthalate, polybutylene terephthalate, polyethylene naphthalate, polybutylene naphthalate, and poly(1,4-cyclohexylenedimethylene terephthalate); polyphenylene ether-based resins; polycarbonate-based resins; polysulfone-based resins; polyamide-based resins; polyvinyl chloride resins; and styrene-based resins. A mixture of these resins (polymer alloy) may also be used.

The aqueous composition, which contains the compound represented by Formula (1) having excellent pharmacological action, can be suitably used as a pharmaceutical, for example. In this case, the target disease is not particularly limited, and may be selected as appropriate depending on the pharmacological action or the like of the compound represented by Formula (1).

Specifically, the aqueous composition can be used, for example, as a prophylactic or therapeutic agent for ocular hypertension or glaucoma, based on the Rho kinase inhibitory action or intraocular pressure-lowering action of the compound represented by Formula (1). More specifically, examples of types of glaucoma include primary open-angle glaucoma, normal-tension glaucoma, hypersecretion glaucoma, acute closed-angle glaucoma, chronic closed-angle glaucoma, plateau iris syndrome, combined mechanism glaucoma, steroid-induced glaucoma, capsular glaucoma, pigmentary glaucoma, amyloid-associated glaucoma, neovascular glaucoma, and malignant glaucoma.

Further, as disclosed in JP-B-5557408, the aqueous composition can be used as a prophylactic or therapeutic agent for ocular fundus diseases (lesions that mainly develop in the retina and/or choroidea; specifically, for example, hypertensive or arteriosclerotic ocular fundus abnormalities, central retinal artery occlusion, retinal vein occlusion such as central retinal vein occlusion or branch retinal vein occlusion, diabetic retinopathy, diabetic macular edema, diabetic maculopathy, Eales disease, congenital retinal vascular abnormalities such as Coats disease, von Hippel disease, pulseless disease, macular diseases (such as central serous chorioretinopathy, cystoid macular edema, age-related macular degeneration, macular hole, myopic macular degeneration, vitreoretinal interface maculopathy, drug-related maculopathy, or heredomacular degeneration), retinal detachment (such as rhegmatogenous, tractional, exudative), retinitis pigmentosa, or retinopathy of prematurity). More preferably, the aqueous composition can be used as a prophylactic or therapeutic agent for diabetic retinopathy, diabetic macular edema, or age-related macular degeneration.

<<The Invention of Embodiments Concerning the Method for Providing an Antiseptic Effect>>

The invention of embodiments concerning the "method for providing an antiseptic effect" will be described next.

The "method for providing an antiseptic effect" refers to a method for providing an aqueous composition with an antiseptic effect. In the method for providing an antiseptic effect, it is determined that an antiseptic effect is present if the antiseptic ability of the target to be evaluated is superior to that of a product not containing both the compound represented by Formula (1) or a salt thereof or a solvate of the compound or the salt thereof and a quaternary ammonium surfactant in combination, regardless of the degree of the effect.

Specifically, in the case of using bacteria (for example, *Pseudomonas aeruginosa*, *Staphylococcus aureus*, and *Escherichia coli*), or fungi (for example, *Candida albicans*) in accordance with the "Preservatives-Effectiveness Tests" in the General Information of the Japanese Pharmacopoeia 16$^{th}$ Edition, for example, it is determined that an antiseptic effect is present if the viable cell count for any one or more microbial species after a given number of days can be confirmed to be less than that for a control not containing both the compound represented by Formula (1) or a salt thereof or a solvate of the compound or the salt thereof and a quaternary ammonium surfactant in combination (as the control, purified water known to be not having an antiseptic effect may be used). In this case, it is confirmed that the aqueous composition has been provided with an antiseptic effect.

Note that the meanings of other terms, the amounts of various components to be incorporated, and the like in the method for providing an antiseptic effect are the same as those described in <<With regard to the invention of embodiments concerning the aqueous composition>> above.

EXAMPLES

The present invention will be described next in more detail with reference to examples; however, the invention is in no way limited to these examples. In the following examples, test examples, or the like, ripasudil monohydrochloride dihydrate can be produced in accordance with the method described in WO2006/057397, for example.

Test Example 1 Examination of Ripasudil for Growth Inhibitory Activity on Microorganisms In order to examine ripasudil for the presence or absence of growth inhibitory activity on microorganisms (bacteria and fungi), the following tests were performed using *Pseudomonas aeruginosa* as a bacterium and *Candida albicans* as a fungus.

<Examination of Growth Inhibitory Activity on *Pseudomonas aeruginosa*>

*Pseudomonas aeruginosa* NBRC 13275 strain was seeded on the soybean-casein digest medium (Merck Corporation) and cultured at 30 to 35° C. for 20 to 22 hours. The culture was then diluted with peptone saline buffer (pH 7.0) to 1,000 CFU/mL or less to obtain a test bacterial suspension.

Two grams of ripasudil monohydrochloride dihydrate were dissolved in 270 mL of phosphate buffer (pH 7.2) to obtain a dilute sample solution.

A sample was obtained by mixing 0.5 mL of the test bacterial suspension with 50 mL of the dilute sample solution (note that a mixture of 0.5 mL of the test bacterial suspension and 50 mL of phosphate buffer (pH 7.2) was used as a control sample).

After a lapse of 30 minutes or longer, the samples were filtered using filters composed of mixed cellulose esters (Millipore Corporation), in accordance with a membrane filter method, to recover the cells on the filters, and then the filters were washed with 100 mL of phosphate buffer (pH 7.2). The resulting filters were placed on the soybean-casein digest agar medium (Merck Corporation) and cultured at 30 to 35° C. for 3 days.

After the culture, the number of colonies formed was counted (note that the test was performed twice, and an average value was determined). From the determined number of colonies, a growth inhibitory ratio (%) was calculated using the following equation:

Growth inhibitory ratio (%)=|(the number of colonies for the control sample−the number of colonies for the sample)|/the number of colonies for the control sample×100

<Examination of Growth Inhibitory Activity on *Candida albicans*>

*Candida albicans* NERC 1594 strain was seeded on the Sabouraud-dextrose liquid medium (Merck Corporation) and cultured at 20 to 25° C. for 44 to 46 hours. The culture was then diluted with peptone saline buffer (pH 7.0) to 1,000 CFU/mL or less to obtain a test bacterial suspension. Using the obtained test bacterial suspension, the same operation as that in the test for *Pseudomonas aeruginosa* described above was performed to recover the cells on the filters. The resulting filters were placed on the Sabouraud-dextrose agar medium (Merck Corporation) and cultured at 20 to 25° C. for 5 days.

After the culture, the number of colonies formed was counted (note that the test was performed twice, and an average value was determined). A growth inhibitory ratio (%) was also calculated.

The results are shown in Table 1.

TABLE 1

|  | Number of Formed Colonies | | Growth Inhibitory Ratio |
| --- | --- | --- | --- |
|  | Sample | Control Sample | |
| *Pseudomonas aeruginosa* | 0 | 47 | 100% |
| *Candida albicans* | 23 | 37 | 37.8% |

The results set forth in Table 1 showed that ripasudil has growth inhibitory activity on both *Pseudomonas aeruginosa* and *Candida albicans*.

The foregoing test results revealed that the compound represented by Formula (1) typified by ripasudil or a salt thereof or a solvate of the compound or the salt thereof has an antiseptic effect against bacteria and fungi.

Test Example 2 Examination of Augmentation of the Antiseptic Effect Through the Combination of Ripasudil and Benzalkonium In order to examine whether the antiseptic effect against microorganisms (bacteria and fungi) is augmented or not through the combination of ripasudil and benzalkonium, the following tests were performed using *Pseudomonas aeruginosa* as a bacterium and *Candida albicans* as a fungus.

Note that it is known that an effective concentration of benzalkonium chloride is from 0.002 to 0.010, and sufficient antimicrobial activity is not demonstrated at a concentration of 0.001% ("Tenganzai (Eye Drops)" published in 1984 by Nanzando Co., Ltd., pages 76-83). In this test, therefore, the presence or absence of synergistic action (synergism) of ripasudil and benzalkonium was examined using such an amount of benzalkonium chloride.

<Examination of Growth Inhibitory Activity on *Pseudomonas aeruginosa*>

*Pseudomonas aeruginosa* NBRC 13275 strain was seeded on the soybean-casein digest agar medium (Merck Corporation) and cultured at 30 to 35° C. for 18 to 24 hours. The cultured cells were then suspended in 0.1% peptone saline buffer (Nihon Pharmaceutical Co., Ltd.) and adjusted to a cell count of about $10^8$ per mL to obtain a test bacterial suspension.

Fifteen milliliters each of the sample preparations prepared using the methods described below were inoculated with 0.1 mL of the test bacterial suspension, and then a sterilized container for eye drops made of polypropylene (volume: 20 mL) was filled therewith, and the sample preparations were preserved under a condition of light shielding at 20 to 25° C. for 14 days.

After the preservation, a series of dilutions were prepared by serially diluting each of the sample preparations every 10-fold with the soybean-casein digest medium (Nihon Pharmaceutical Co., Ltd.) supplemented with lecithin-polysorbate 80, and poured into the soybean-casein digest agar medium (Nihon Pharmaceutical Co., Ltd.) supplemented with lecithin-polysorbate 80 in accordance with a petri-plate method and cultured at 30 to 35° C. for 5 days.

After the culture, the viable cell count per mL of each of the sample preparations was determined from the number of formed colonies and the dilution factor.

<Examination of Growth Inhibitory Activity on *Candida albicans*>

*Candida albicans* NBRC 1594 strain was seeded on the Sabouraud-dextrose agar medium (Merck Corporation) and cultured at 20 to 25° C. for 40 to 48 hours. The cultured cells were then suspended in 0.1% peptone saline buffer (Nihon Pharmaceutical Co., Ltd.) and adjusted to a cell count of about $10^8$ per mL to obtain a test bacterial suspension. Using the obtained test bacterial suspension, the same operation as that in the test for *Pseudomonas aeruginosa* described above was performed, and each of the sample preparations inoculated with the test bacterial suspension was preserved.

After the preservation, a series of dilutions were prepared by serially diluting each of the sample preparations every 10-fold with the soybean-casein digest medium (Nihon Pharmaceutical Co., Ltd.) supplemented with lecithin-polysorbate 80, and poured into the Sabouraud-dextrose agar medium (Nihon Pharmaceutical Co., Ltd.) supplemented with lecithin-polysorbate 80 in accordance with the petri-plate method and cultured at 20 to 25° C. for 5 days.

After the culture, the viable cell count per mL of each of the sample preparations was determined from the number of formed colonies and the dilution factor.

Note that as the sample preparations, two types of sample preparations, i.e., a sample preparation containing ripasudil alone and a sample preparation containing ripasudil and benzalkonium, were used.

<Sample Preparation Containing Ripasudil Alone>

An aqueous composition containing, per 100 mL, 0.4896 g of ripasudil monohydrochloride dihydrate (0.4 g, as the free form of ripasudil), 0.4 g of anhydrous sodium dihydrogen phosphate, 2.136 g of glycerin, an appropriate amount of sodium hydroxide (pH 6.0), and sterile purified water (balance) was prepared, and this aqueous composition was sterilized through a filter to obtain a sample preparation.

<Sample Preparation Containing Ripasudil and Benzalkonium>

An aqueous composition containing, per 100 mL, 0.4896 g of ripasudil monohydrochioride dihydrate (0.4 g, as the free form of ripasudil), 0.001 g (0.001 w/v %) of benzalkonium chloride, 0.4 g of anhydrous sodium dihydrogen phosphate, 2.136 g of glycerin, an appropriate amount of sodium hydroxide (pH 6.0), and sterile purified water (balance) was prepared, and this aqueous composition was sterilized through a filter to obtain a sample preparation.

The results are shown in Table 2. Note that the cell count of the inoculum was converted into the viable cell count per mL of the sample, from the viable cell count in the test bacterial suspension at the time of inoculation.

TABLE 2

| | | Viable Cell Count per mL of the Sample | | Ripasudil + |
|---|---|---|---|---|
| | | Ripasudil Alone | Ripasudil + Benzalkonium | Benzalkonium/ Ripasudil Alone |
| *Pseudomonas aeruginosa* | Inoculum Cell Count | 1300000 | | — |
| | After Preservation of 14 Days | 380000 | <10 | <1/38000 |
| *Candida albicans* | Inoculum Cell Count | 930000 | | — |
| | After Preservation of 14 Days | 57000 | 120 | 1/475 |

As seen from the results set forth in Table 2, the combination of ripasudil and an amount of benzalkonium chloride that is known to be not demonstrating sufficient antimicrobial activity reduced the viable cell count of *Pseudomonas aeruginosa* to less than 1/38,000, and the viable cell count of *Candida albicans* to 1/475, compared to ripasudil alone.

The foregoing test results revealed that the combination of the compound represented by Formula (1) typified by ripasudil or a salt thereof or a solvate of the compound or the salt thereof and a quaternary ammonium surfactant typified by benzalkonium synergistically augments the antiseptic effect, and an excellent antiseptic effect is achieved even if the amount of the quaternary ammonium surfactant corresponds to an amount of the quaternary ammonium surfactant alone that does not demonstrate an antiseptic effect.

[Test Example 3] Examination of Augmentation of the Antiseptic Effect Through the Combination of Ripasudil and Benzalkonium No. 2

The test was performed as in Test Example 2, except that *Staphylococcus aureus* (NBRC 13276 strain) was used as a bacterium instead of *Pseudomonas aeruginosa*.

The results are shown in Table 3.

TABLE 3

| | | Viable Cell Count per mL of the Sample | | Ripasudil + |
|---|---|---|---|---|
| | | Ripasudil Alone | Ripasudil + Benzalkonium | Benzalkonium/ Ripasudil Alone |
| *Staphylococcus aureus* | Inoculum Cell Count | 1600000 | | — |
| | After Preservation of 14 Days | 200 | <10 | <1/20 |

As seen from the results set forth in Table 3, the combination of ripasudil and an amount of benzalkonium chloride that is known to be not demonstrating sufficient antimicrobial activity reduced the viable cell count of *Staphylococcus aureus* to less than 1/20, compared to ripasudil alone.

Test Example 4 Examination of Augmentation of the Antiseptic Effect Through the Combination of Ripasudil and Benzalkonium No. 3

The test was performed as in Test Example 2, except that *Escherichia coli* (NBRC 3972 strain) was used as a bacterium instead of *Pseudomonas aeruginosa*, and the preservation period was changed to a period of 28 days.

The results are shown in Table 4.

TABLE 4

|  |  | Viable Cell Count per mL of the Sample | | Ripasudil + Benzalkonium/ Ripasudil Alone |
|---|---|---|---|---|
|  |  | Ripasudil Alone | Ripasudil + Benzalkonium | |
| *Escherichia coli* | Inoculum Cell Count | 1600000 | — | |
|  | After Preservation of 28 Days | 1400000 | <10 | <1/140000 |

As seen from the results set forth in Table 4, the combination of ripasudil and an amount of benzalkonium chloride that is known to be not demonstrating sufficient antimicrobial activity reduced the viable cell count of *Escherichia coli* to less than 1/140,000, compared to ripasudil alone.

The results set forth in Tables 3 and 4 revealed that the combination of ripasudil and benzalkonium exhibits augmentation of the growth inhibitory activity not only on *Pseudomonas aeruginosa* and *Candida albicans* but also on a wide range of microorganisms.

The foregoing test results revealed that the combination of the compound represented by Formula (1) typified by ripasudil or a salt thereof or a solvate of the compound or the salt thereof and a quaternary ammonium surfactant typified by benzalkonium exhibits remarkable augmentation of the antiseptic effect on a wide range of microorganisms.

Production Examples 1 to 27

Eye drops containing the components in the quantities (amounts (g) per 100 mL of the aqueous composition) shown in Tables 5 to 7 can be produced in accordance with a conventional method.

TABLE 5

| | Production Example 1 | Production Example 2 | Production Example 3 | Production Example 4 | Production Example 5 | Production Example 6 | Production Example 7 | Production Example 8 | Production Example 9 |
|---|---|---|---|---|---|---|---|---|---|
| Ripasudil Monohydrochloride Dihydrate (as the amount of the free form) | 0.2 | 0.2 | 0.2 | 0.4 | 0.4 | 0.4 | 0.8 | 0.8 | 0.8 |
| Benzalkonium Chloride | 0.001 | 0.005 | 0.01 | 0.001 | 0.005 | 0.01 | 0.001 | 0.005 | 0.01 |
| Sodium Chloride | 0.65 | | | | 0.3 | 0.3 | 0.3 | 0.3 | |
| Glycerin | | 2 | | | 1 | | | 0.5 | 1 |
| Propylene Glycol | | | 2 | | | 1 | | 0.5 | 1 |
| Potassium Chloride | | | | 0.6 | | | 0.3 | | |
| Boric Acid | | | | | | | | | |
| Borax | | | | | | | | | |
| Sodium Dihydrogenphosphate Monohydrate | 0.4 | 0.4 | 0.4 | | | 0.4 | 0.4 | 0.4 | 0.4 |
| Dibasic Sodium Phosphate Hydrate | | | | | | | | q.s. | q.s. |
| Anhydrous Sodium Monohydrogen Phosphate | | | | | | q.s. | q.s. | | |
| Potassium Dihydrogenphosphate | | | | 0.4 | 0.4 | | | | |
| Sodium Hydroxide | q.s. | q.s. | q.s. | q.s. | q.s. | | | | |
| Trometamol | | | | | | | | | |
| Hydrochloric Acid | | | | | | | | | |
| Citric Acid Hydrate | 0.1 | | | | | 0.1 | | | |
| Sodium Acetate Hydrate | | 0.1 | | | | 0.1 | | | |
| Sodium Edetate | | | | 0.1 | | | 0.1 | | |
| Methyl Parahydroxybenzoate | | | 0.01 | | | | 0.01 | | |
| Propyl Parahydroxybenzoate | | | 0.01 | | | | 0.01 | | |
| Chlorobutanol | | | | 0.2 | | | | 0.2 | |
| Polysorbate 80 | 0.3 | | | 0.3 | 0.3 | | | 0.3 | 0.3 |
| Polyoxyethylene Castor Oil 60 | | 0.3 | | 0.3 | | 0.3 | | 0.3 | 0.3 |
| Polyethylene Glycol Monostearate | | | 1.5 | 1.5 | | | 1.5 | | 1.5 |
| Purified Water | Total Amount 100 mL | Total Amount 100 mL | Total Amount 100 mL | Total Amount 100 mL | Total Amount 100 mL | Total Amount 100 mL | Total Amount 100 mL | Total Amount 100 mL | Total Amount 100 mL |
| pH | 5 | 5 | 6 | 6 | 6.5 | 6.5 | 7 | 7 | 8 |

TABLE 6

| | Production Example 10 | Production Example 11 | Production Example 12 | Production Example 13 | Production Example 14 | Production Example 15 | Production Example 16 | Production Example 17 | Production Example 18 |
|---|---|---|---|---|---|---|---|---|---|
| Ripasudil Monohydrochloride Dihydrate (as the amount of the free form) | 0.2 | 0.2 | 0.2 | 0.4 | 0.4 | 0.4 | 0.8 | 0.8 | 0.8 |
| Benzalkonium Chloride | 0.001 | 0.005 | 0.01 | 0.001 | 0.005 | 0.01 | 0.001 | 0.005 | 0.01 |
| Sodium Chloride | 0.65 | | | | 0.3 | 0.3 | 0.3 | 0.3 | |
| Glycerin | | 2 | | | 1 | | | 0.5 | 1 |
| Propylene Glycol | | | 2 | | | 1 | | 0.5 | 1 |
| Potassium Chloride | | | | 0.6 | | | 0.3 | | |
| Boric Acid | 1.0 | 1.0 | 1.0 | 1.0 | 1.0 | 1.0 | 1.0 | 1.0 | 1.0 |
| Borax | | | | | q.s. | q.s. | q.s. | q.s. | q.s. |
| Sodium Dihydrogenphosphate Monohydrate | | | | | | | | | |
| Dibasic Sodium Phosphate Hydrate | | | | | | | | | |
| Anhydrous Sodium Monohydrogen Phosphate | | | | | | | | | |
| Potassium Dihydrogenphosphate | | | | | | | | | |
| Sodium Hydroxide | q.s. | q.s. | q.s. | q.s. | | | | | |
| Trometamol | | | | | | | | | |
| Hydrochloric Acid | | | | | | | | | |
| Citric Acid Hydrate | 0.1 | | | | | 0.1 | | | |
| Sodium Acetate Hydrate | | 0.1 | | | | 0.1 | | | |
| Sodium Edetate | | | | 0.1 | | | 0.1 | | |
| Methyl Parahydroxybenzoate | | | 0.01 | | | | | 0.01 | |
| Propyl Parahydroxybenzoate | | | 0.01 | | | | | 0.01 | |
| Chlorobutanol | | | | 0.2 | | | | 0.2 | |
| Polysorbate 80 | 0.3 | | | 0.3 | 0.3 | | | 0.3 | 0.3 |
| Polyoxyethylene Castor Oil 60 | | 0.3 | | 0.3 | | 0.3 | | 0.3 | 0.3 |
| Polyethylene Glycol Monostearate | | | 1.5 | 1.5 | | | 1.5 | | 1.5 |
| Purified Water | Total Amount 100 mL | Total Amount 100 mL | Total Amount 100 mL | Total Amount 100 mL | Total Amount 100 mL | Total Amount 100 mL | Total Amount 100 mL | Total Amount 100 mL | Total Amount 100 mL |
| pH | 5 | 5 | 6 | 6 | 6.5 | 6.5 | 7 | 7 | 8 |

TABLE 7

| | Production Example 19 | Production Example 20 | Production Example 21 | Production Example 22 | Production Example 23 | Production Example 24 | Production Example 25 | Production Example 26 | Production Example 27 |
|---|---|---|---|---|---|---|---|---|---|
| Ripasudil Monohydrochloride Dihydrate (as the amount of the free form) | 0.2 | 0.2 | 0.2 | 0.4 | 0.4 | 0.4 | 0.8 | 0.8 | 0.8 |
| Benzalkonium Chloride | 0.001 | 0.005 | 0.01 | 0.001 | 0.005 | 0.01 | 0.001 | 0.005 | 0.01 |
| Sodium Chloride | 0.65 | | | | 0.3 | 0.3 | 0.3 | 0.3 | |
| Glycerin | | 2 | | | 1 | | | 0.5 | 1 |
| Propylene Glycol | | | 2 | | | 1 | | 0.5 | 1 |
| Potassium Chloride | | | | 0.6 | | | 0.3 | | |
| Boric Acid | | | | | | | | | |
| Borax | | | | | | | | | |
| Sodium Dihydrogenphosphate Monohydrate | | | | | | | | | |
| Dibasic Sodium Phosphate Hydrate | | | | | | | | | |
| Anhydrous Sodium Monohydrogen Phosphate | | | | | | | | | |
| Potassium Dihydrogenphosphate | | | | | | | | | |
| Sodium Hydroxide | | | | | | | | | |
| Trometamol | 1.5 | 1.5 | 1.5 | 1.5 | 1.5 | 1.5 | 1.5 | 1.5 | 1.5 |
| Hydrochloric Acid | q.s. | q.s. | q.s. | q.s. | q.s. | q.s. | q.s. | q.s. | q.s. |
| Citric Acid Hydrate | 0.1 | | | | | 0.1 | | | |
| Sodium Acetate Hydrate | | 0.1 | | | | 0.1 | | | |

TABLE 7-continued

| | Production Example 19 | Production Example 20 | Production Example 21 | Production Example 22 | Production Example 23 | Production Example 24 | Production Example 25 | Production Example 26 | Production Example 27 |
|---|---|---|---|---|---|---|---|---|---|
| Sodium Edetate | | | | 0.1 | | | 0.1 | | |
| Methyl Parahydroxybenzoate | | 0.01 | | | | | 0.01 | | |
| Propyl Parahydroxybenzoate | | 0.01 | | | | | 0.01 | | |
| Chlorobutanol | | | | 0.2 | | | | 0.2 | |
| Polysorbate 80 | 0.3 | | | 0.3 | 0.3 | | | 0.3 | 0.3 |
| Polyoxyethylene Castor Oil 60 | | 0.3 | | 0.3 | | 0.3 | | 0.3 | 0.3 |
| Polyethylene Glycol Monostearate | | | 1.5 | 1.5 | | | 1.5 | | 1.5 |
| Purified Water | Total Amount 100 mL | Total Amount 100 mL | Total Amount 100 mL | Total Amount 100 mL | Total Amount 100 mL | Total Amount 100 mL | Total Amount 100 mL | Total Amount 100 mL | Total Amount 100 mL |
| pH | 5 | 5 | 6 | 6 | 6.5 | 6.5 | 7 | 7 | 8 |

Production Examples 28 to 54

Eye drops of Production Examples 28 to 54 can be produced as in Production Examples 1 to 27, using an equal amount of benzethonium chloride instead of benzalkonium chloride, in accordance with a conventional method.

Production Examples 55 to 108

Eye drops of Production Examples 55 to 108 can be produced in accordance with a conventional method as in Production Examples 1 to 54, except that instead of ripasudil monohydrochloride dihydrate, an equal amount of 4-bromo-5-[[(2S)-2-methyl-1,4-diazepan-1-yl]sulfonyl]isoquinoline is used.

INDUSTRIAL APPLICABILITY

In accordance with the present invention, an aqueous composition containing the compound represented by Formula (1) having excellent pharmacological action, and having an excellent antiseptic effect and good preservation stability can be provided, and the aqueous composition can be advantageously used in the pharmaceutical industry, for example.

The invention claimed is:

1. An aqueous composition, comprising:
   ripasudil, or a salt thereof, or a solvate of ripasudil or the salt thereof; and
   benzalkonium chloride,
   wherein the composition does not contain brinzolamide,
   and wherein a content of the benzalkonium chloride is from 0.0002 part by mass to 0.0025 part by mass, relative to 1 part by mass of the ripasudil, or a salt thereof, or a solvate of ripasudil or the salt thereof.

2. The aqueous composition according to claim 1, wherein the aqueous composition is an eye drop.

3. A method for producing an aqueous composition with an antiseptic effect, the method comprising:
   incorporating ripasudil, or a salt thereof, or a solvate of ripasudil or the salt thereof and benzalkonium chloride into the aqueous composition,
   wherein the aqueous composition does not contain brinzolamide,
   and wherein a content of the benzalkonium chloride is from 0.0002 part by mass to 0.0025 part by mass, relative to 1 part by mass of the ripasudil, or a salt thereof, or a solvate of ripasudil or the salt thereof.

4. The method according to claim 3, wherein the aqueous composition is an eye drop.

5. The aqueous composition according to claim 1, wherein a content of the benzalkonium chloride is from 0.00005 to 0.002 w/v %, based on the total volume of the aqueous composition.

6. The aqueous composition according to claim 1, wherein a content of the benzalkonium chloride is from 0.0001 to 0.002 w/v %, based on the total volume of the aqueous composition.

7. The aqueous composition according to claim 6, wherein a content of the ripasudil or a salt thereof, or a solvate of ripasudil or the salt thereof, is from 0.01 to 10 w/v %, calculated as the free form, based on the total volume of the aqueous composition.

8. The aqueous composition according to claim 6, wherein a content of the ripasudil or a salt thereof, or a solvate of ripasudil or the salt thereof, is from 0.05 to 5 w/v %, calculated as the free form, based on the total volume of the aqueous composition.

9. The aqueous composition according to claim 1, wherein the composition does not contain nipradilol and bunazosin.

* * * * *